(12) United States Patent
Okuma

(10) Patent No.: US 9,101,392 B2
(45) Date of Patent: Aug. 11, 2015

(54) INFORMATION READER OF INJECTION CONTAINER

(71) Applicant: Ookuma Electronic Co., Ltd., Kumamoto-shi (JP)

(72) Inventor: Keiji Okuma, Kumamoto (JP)

(73) Assignee: Ookuma Electronic Co., Ltd., Kumamoto-shi (JP)

(*) Notice: Subject to any disclaimer, the term of this patent is extended or adjusted under 35 U.S.C. 154(b) by 257 days.

(21) Appl. No.: 13/673,399

(22) Filed: Nov. 9, 2012

(65) Prior Publication Data

US 2014/0131534 A1 May 15, 2014

(51) Int. Cl.
| | |
|---|---|
| A61J 1/14 | (2006.01) |
| A61B 19/00 | (2006.01) |
| B65B 3/00 | (2006.01) |
| F16M 13/02 | (2006.01) |
| A61J 1/00 | (2006.01) |
| B65C 3/10 | (2006.01) |
| A61M 5/00 | (2006.01) |

(52) U.S. Cl.
CPC . *A61B 19/44* (2013.01); *A61J 1/00* (2013.01); *A61J 1/14* (2013.01); *A61M 5/00* (2013.01); *B65B 3/003* (2013.01); *B65B 3/006* (2013.01); *B65C 3/10* (2013.01); *F16M 13/022* (2013.01); *A61B 2019/442* (2013.01); *A61J 2205/10* (2013.01); *G06K 2209/01* (2013.01)

(58) Field of Classification Search
CPC .......... A61J 1/14; A61J 3/00; A61J 2205/10; B65B 3/003; B65B 3/006; B65C 3/10; F16M 13/022; A61B 19/44
USPC ........ 248/230.3, 230.5, 228.3, 228.5, 231.41, 248/231.61, 213.2; 404/108; 222/415
See application file for complete search history.

(56) References Cited

U.S. PATENT DOCUMENTS

| | | | | |
|---|---|---|---|---|
| 4,878,705 | A * | 11/1989 | Arnquist | 294/116 |
| 5,093,978 | A * | 3/1992 | Binder | 483/43 |
| 5,549,444 | A * | 8/1996 | Dubuit | 414/796.7 |
| 5,584,814 | A * | 12/1996 | Schuster et al. | 604/187 |
| RE35,605 | E * | 9/1997 | Nomaru et al. | 294/119.1 |
| 6,116,118 | A * | 9/2000 | Wesch, Jr. | 81/57.34 |
| 6,604,903 | B2 * | 8/2003 | Osborne et al. | 414/411 |
| 6,813,868 | B2 * | 11/2004 | Baldwin et al. | 53/411 |
| 6,820,849 | B2 * | 11/2004 | Kennard | 248/231.61 |

(Continued)

FOREIGN PATENT DOCUMENTS

JP 2010-115339 5/2010

*Primary Examiner* — Terrell McKinnon
*Assistant Examiner* — Eret McNichols
(74) *Attorney, Agent, or Firm* — Jordan and Hamburg LLP

(57) ABSTRACT

An information reader of an injection container that includes a container clamping mechanism clamping side portions of the injection container, the container clamping mechanism includes a pair of first clamping bodies arranged on one side of the side portions of the injection container, and a second clamping body capable of entering between the pair of the first clamping bodies. Each of the pair of the first clamping bodies includes a first clamping unit having a first recess in an approximate doglegged shape, and a first arm portion projecting approximately horizontally from a lower end portion of the first clamping unit. The second clamping body includes a second clamping unit having a second recess in an approximately reverse doglegged shape formed to face against the first recess, and a second arm portion projecting approximately horizontally from a lower end portion of the second clamping unit.

1 Claim, 11 Drawing Sheets

(56) References Cited

U.S. PATENT DOCUMENTS

| | | | |
|---|---|---|---|
| 6,986,234 B2* | 1/2006 | Liedtke | 53/399 |
| 7,007,443 B2* | 3/2006 | Liedtke et al. | 53/399 |
| 7,565,782 B2* | 7/2009 | Williams et al. | 53/237 |
| 7,614,942 B2* | 11/2009 | Liermann et al. | 452/186 |
| 8,104,521 B2* | 1/2012 | Luchinger et al. | 141/83 |
| 8,267,129 B2* | 9/2012 | Doherty et al. | 141/330 |
| 8,271,138 B2* | 9/2012 | Eliuk et al. | 700/260 |
| 8,865,070 B2* | 10/2014 | Giribona et al. | 422/65 |
| 2002/0020459 A1* | 2/2002 | Baldwin et al. | 141/11 |
| 2004/0154690 A1* | 8/2004 | Osborne et al. | 141/27 |
| 2004/0168741 A1* | 9/2004 | Baldwin | 141/98 |
| 2004/0241041 A1* | 12/2004 | Woodworth et al. | 422/22 |
| 2004/0261358 A1* | 12/2004 | Liedtke | 53/399 |
| 2008/0114328 A1* | 5/2008 | Doherty et al. | 604/414 |
| 2008/0169046 A1* | 7/2008 | Bender et al. | 141/11 |
| 2008/0203255 A1* | 8/2008 | Workman et al. | 248/231.61 |
| 2008/0230552 A1* | 9/2008 | Williams et al. | 221/5 |
| 2009/0067973 A1* | 3/2009 | Eliuk et al. | 414/729 |
| 2011/0067781 A1* | 3/2011 | Osborne | 141/37 |
| 2012/0048675 A1* | 3/2012 | Giribona et al. | 198/346.2 |
| 2012/0048676 A1* | 3/2012 | Giribona et al. | 198/346.2 |
| 2012/0051971 A1* | 3/2012 | Giribona et al. | 422/63 |

* cited by examiner

INFORMATION READER OF INJECTION CONTAINER

BACKGROUND OF THE INVENTION

The present invention relates to an information reader of an injection container to read information on a label attached on an outer peripheral surface of the injection container in a substantially tubular shape.

Conventionally, in medical settings such as hospitals, drug price points are summed up based on drug names, doses and the like described in the so-called charts, and drug costs are charged to insurers of health insurance and the like based on the summed value. This also applies to injections used in the medical settings.

At the time of surgical operations in particular, the injections are prepared in advance based on, for example, names and numbers of the injections described in the charts. During the surgical operation, however, additional injections or injections other than those described in the charts and the like may be required. However, it is quite troublesome and difficult for staff during the surgical operation to record each of the injection names every time they are required in such an urgent manner. Keeping the injections that are prepared in advance and the injections that are needed urgently in separate places, for example, is also quite difficult for the staff concentrating attention on the surgical operation.

Therefore, a list is made after the surgical operation, for example, by manually reading labels of all injection containers, and the list is compared with the injection names described in the charts in advance, so as to select the injections that were required urgently. Such selecting operation includes, for example, picking up each of the injection containers having various shapes and reading the information on the labels attached to the outer peripheral surfaces, which are troublesome and difficult work.

Thus, there is a problem in that an increase in man-hour accompanied by such selecting operation imposes a heavy burden on the medical settings where the number of the staff, such as nurses, is limited. There is also a problem of reading mistakes due to human errors, because the selecting operation depends on the eyesight.

In order to solve such problems, for example, an information reader of an empty injection container by the present inventor is known (refer to Japanese Unexamined Patent Application Publication No. 2010-115339).

SUMMARY OF THE INVENTION

Japanese Unexamined Patent Application Publication No. 2010-115339 relates to an information reader of an empty injection container that reads information on a label attached on an outer peripheral surface of the empty injection container in a substantially tubular shape by rotating the empty injection container about a substantially central axis in its cylinder length direction. As shown in FIG. 4 to FIG. 6 thereof, there are disclosed a pair of first clamping bodies arranged to face each other and separate in a longitudinal direction, each of which is formed by a plate body that has a first bending side in a doglegged shape concavely formed on an upper side of a rectangular plate member and that is arranged by making its plate surface almost orthogonal to a cylinder direction, a second clamping body arranged in approximately parallel to the first clamping bodies, which is formed by a plate body that has a second bending side in a doglegged shape concavely formed to face against the first bending sides and that is formed to be able to enter between the pair of the first clamping bodies, and a driving mechanism that allows the pair of the first clamping bodies to advance or retreat in a horizontal direction that is almost orthogonal to the cylinder direction, and allows the second clamping body to advance or retreat in the direction opposite to the advancing or retreating direction. Disclosed technique is that the driving mechanism allows the pair of the first clamping bodies and the second clamping body, substantially facing each other, to move approachingly and separatingly, and at the time of approaching, the pair of the first bending sides and the second bending side clamp side portions of the empty injection container.

Further, according to Japanese Unexamined Patent Application Publication No. 2010-115339, the driving mechanism includes a first rack gear in an approximately horizontal direction that is provided at a bottom side of at least one of the pair of the first clamping bodies, a pinion gear engaging with the first rack gear, a driving unit for rotating the pinion gear, and a second rack gear that is provided at the second clamping body and engages with the pinion gear while being arranged to face against the first rack gear with the pinion gear therebetween.

Thus, with the information reader of the empty injection container according to Japanese Unexamined Patent Application Publication No. 2010-115339, plate surfaces at lower sides of the pair of the first clamping bodies and the second clamping body overlap with each other when they are brought closer by the driving mechanism, as shown in FIG. 5 thereof.

However, as the injection containers may be made of glass, for example, it is likely that glass fragments and the like are generated in the information reader of the empty injection container. As the injection containers that were used in an operating room and the like are introduced into the information reader of the empty injection container, it is also likely that fiber wastes and the like generated in the operating room may be introduced into the information reader of the empty injection container.

As a result, such fragments and wastes may enter between the first clamping bodies and the second clamping body that are overlapped with each other as described above. This may cause a problem in that, due to the effect of the fragments and the like, such operational malfunctions may be caused that advancing or retreating movement of the pair of the first clamping bodies and the second clamping body is limited and the clamping of the injection container is prohibited.

Especially, when side portions of an ampule or the like with the short cylinder length are to be clamped, for example, it is necessary to reduce the thickness of the first clamping bodies and the second clamping body, or to narrow the space between the first clamping bodies and the second clamping body as much as possible. This may cause a problem in that the operational malfunctions are easily caused due to the influence of the fragments and the like, as the space between the first clamping bodies and the second clamping body narrows.

The present invention is made in view of the above problems in the conventional art, and it is an object of the present invention to provide an information reader of an injection container capable of suppressing operational malfunctions due to fragments, wastes and the like in the device.

According to a first aspect of the present invention, an information reader of an injection container to read information attached on an outer peripheral surface of the injection container in a tubular shape includes a container clamping mechanism removably clamping side portions of the injection container whose cylinder length direction is made approximately horizontal. The container clamping mechanism includes a pair of first clamping bodies arranged on one side of the side portions of the injection container and arranged to face each other while separating in the cylinder length direction, a second clamping body arranged on another side of the side portions of the injection container and capable of entering between the pair of the first clamping bodies, and a driving mechanism allowing the pair of the first clamping bodies to advance or retreat in a direction that is the horizontal direction and is almost orthogonal to the cylinder length direction, and allowing the second clamping body to advance or retreat in a direction opposite to the direction of advancing or retreating of the first clamping bodies. Each of the pair of the first clamping bodies includes a first clamping unit having a first recess in an approximately doglegged shape that bends toward a direction allowing a vertex to separate from the side portion when viewed from the cylinder length direction, and a first arm portion projecting approximately horizontally from a lower end portion of the first clamping unit in a direction opposite to the first recess, with its upper edge continuing to a lower end of the first recess. The second clamping body includes a second clamping unit having a second recess in an approximately reverse doglegged shape formed to face against the first recess, and a second arm portion projecting approximately horizontally from a lower end portion of the second clamping unit in a direction opposite to the second recess, with its upper edge continuing to a lower end of the second recess. The driving mechanism allows the pair of the first clamping bodies and the second clamping body that are substantially facing each other to move approachingly and separatingly, and, at a time of approaching, the first arm portion and the second arm portion are overlapped to support the injection container from below.

According to a second aspect of the information reader of the injection container of the first aspect, the driving mechanism includes an endless belt suspended in the direction of advancing or retreating. Each of the pair of the first clamping bodies includes a first leg portion at the lower end portion of the first clamping unit and near an end opposite to the first arm portion. The second clamping body includes a second lea portion at the lower end portion of the second clamping unit and near an end opposite to the second arm portion. The pair of the first leg portions and the second leg portion are respectively connected to the endless belt at opposing positions with a center of rotation therebetween.

According to the present invention, an information reader of an injection container to read information attached on an outer peripheral surface of the injection container in a tubular shape includes a container clamping mechanism removably clamping side portions of the injection container whose cylinder length direction is made approximately horizontal. The container clamping mechanism includes a pair of first clamping bodies arranged on one side of the side portions of the injection container and arranged to face each other while separating in the cylinder length direction, a second clamping body arranged on another side of the side portions of the injection container and capable of entering between the pair of the first clamping bodies, and a driving mechanism allowing the pair of the first clamping bodies to advance or retreat in a direction that is the horizontal direction and is almost orthogonal to the cylinder length direction, and allowing the second clamping body to advance or retreat in a direction opposite to the direction of advancing or retreating of the first clamping bodies. Each of the pair of the first clamping bodies includes a first clamping unit having a first recess in an approximately doglegged shape that bends toward a direction allowing a vertex to separate from the side portion when viewed from the cylinder length direction, and a first arm portion projecting approximately horizontally from a lower end portion of the first clamping unit in a direction opposite to the first recess, with its upper edge continuing to a lower end of the first recess. The second clamping body includes a second clamping unit having a second recess in an approximately reverse doglegged shape formed to face against the first recess, and a second arm portion projecting approximately horizontally from a lower end portion of the second clamping unit in a direction opposite to the second recess, with its upper edge continuing to a lower end of the second recess. The driving mechanism allows the pair of the first clamping bodies and the second clamping body that are substantially facing each other to move approachingly and separatingly, and, at a time of approaching, the first arm portion and the second arm portion are overlapped to support the injection container from below. As the area where the pair of the first clamping bodies and the second clamping body overlap with each other, at the time of clamping the side portions of the injection container, mainly consists of the area where the first arm portion and the second arm portion, arranged at the same height, overlap with each other, it is possible to reduce the area where the pair of the first clamping bodies and the second clamping body overlap with each other at the time of clamping the side portions of the injection container. Namely, the area between the first clamping bodies and the second clamping body, into which fragments and wastes enter, can be reduced in the device, which makes it possible to provide the information reader of the injection container capable of suppressing operational malfunctions due to the fragments, wastes and the like in the device.

Further, the driving mechanism includes an endless belt suspended in the direction of advancing or retreating. Each of the pair of the first clamping bodies includes a first leg portion at the lower end portion of the first clamping unit and near an end opposite to the first arm portion. The second clamping body includes a second leg portion at the lower end portion of the second clamping unit and near an end opposite to the second arm portion. The pair of the first leg portions and the second leg portion are respectively connected to the endless belt at opposing positions with a center of rotation therebetween. As the driving mechanism allows the pair of the first clamping bodies and the second clamping body that are substantially facing each other to move approachingly and separatingly almost at the same time, the container clamping mechanism can clamp the injection container of the injection container efficiently. Also, the container clamping mechanism can be manufactured with simple components at low cost.

DETAILED DESCRIPTION OF THE INVENTION

Hereinafter, an example of preferred embodiments of the present invention will be explained with reference to FIG. 1 to FIG. 6.

Figure 1:
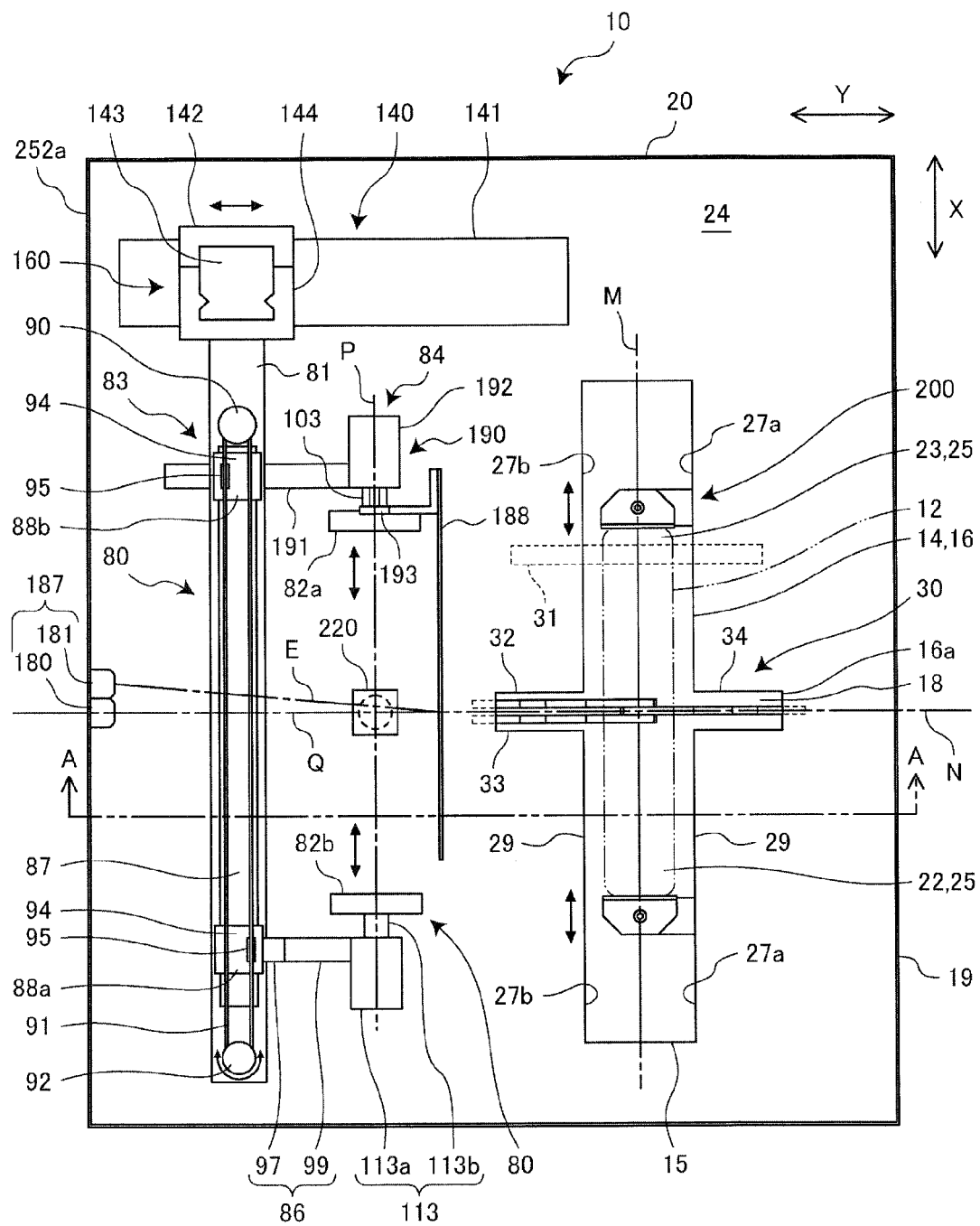
FIG. 1 is an explanatory plan view of an information reader of an injection container according to this embodiment.
Figure 2:
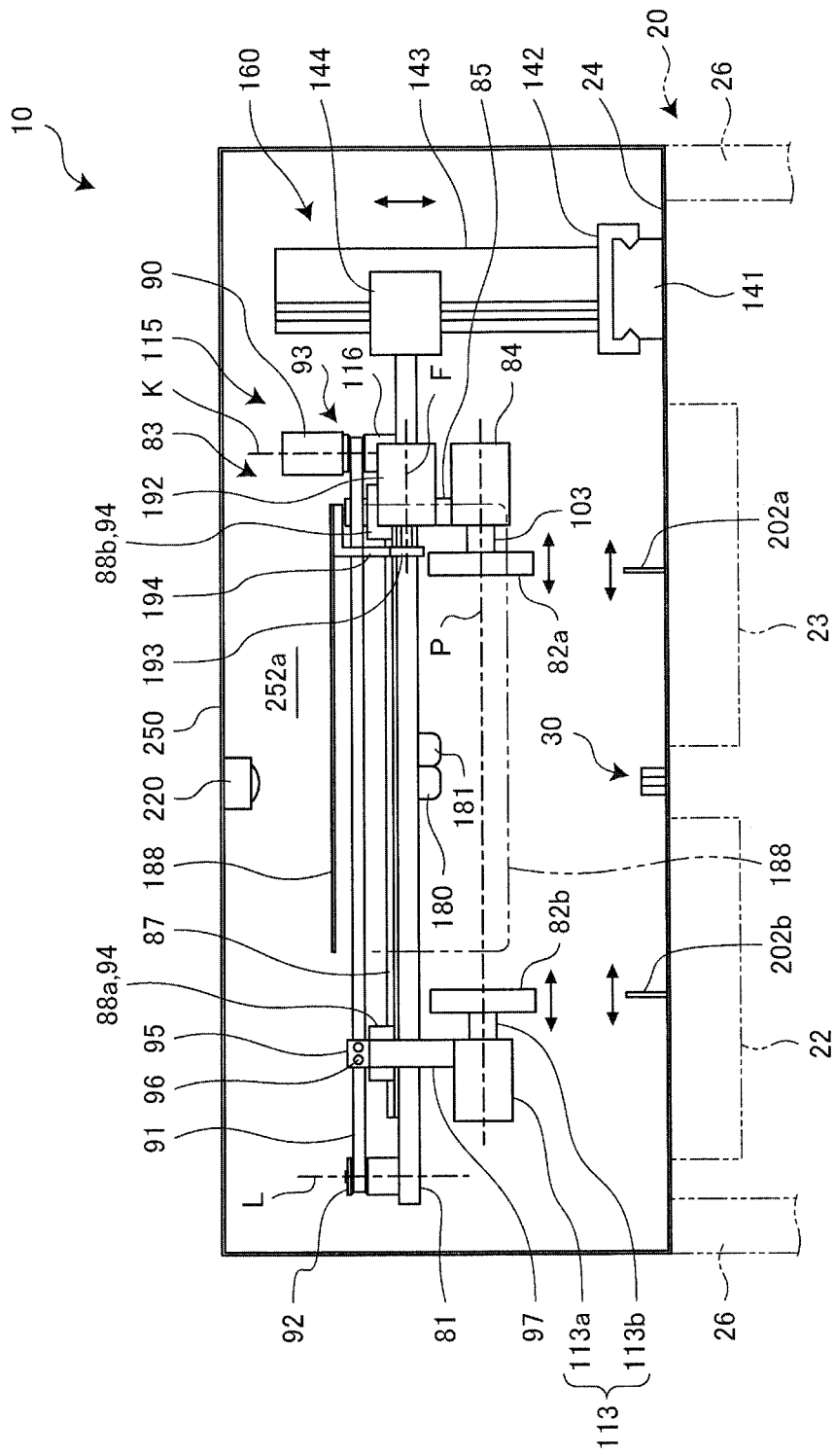
FIG. 2 is an explanatory view showing the right side surface of the information reader of the injection container according to this embodiment, with a part thereof being omitted.
Figure 3:
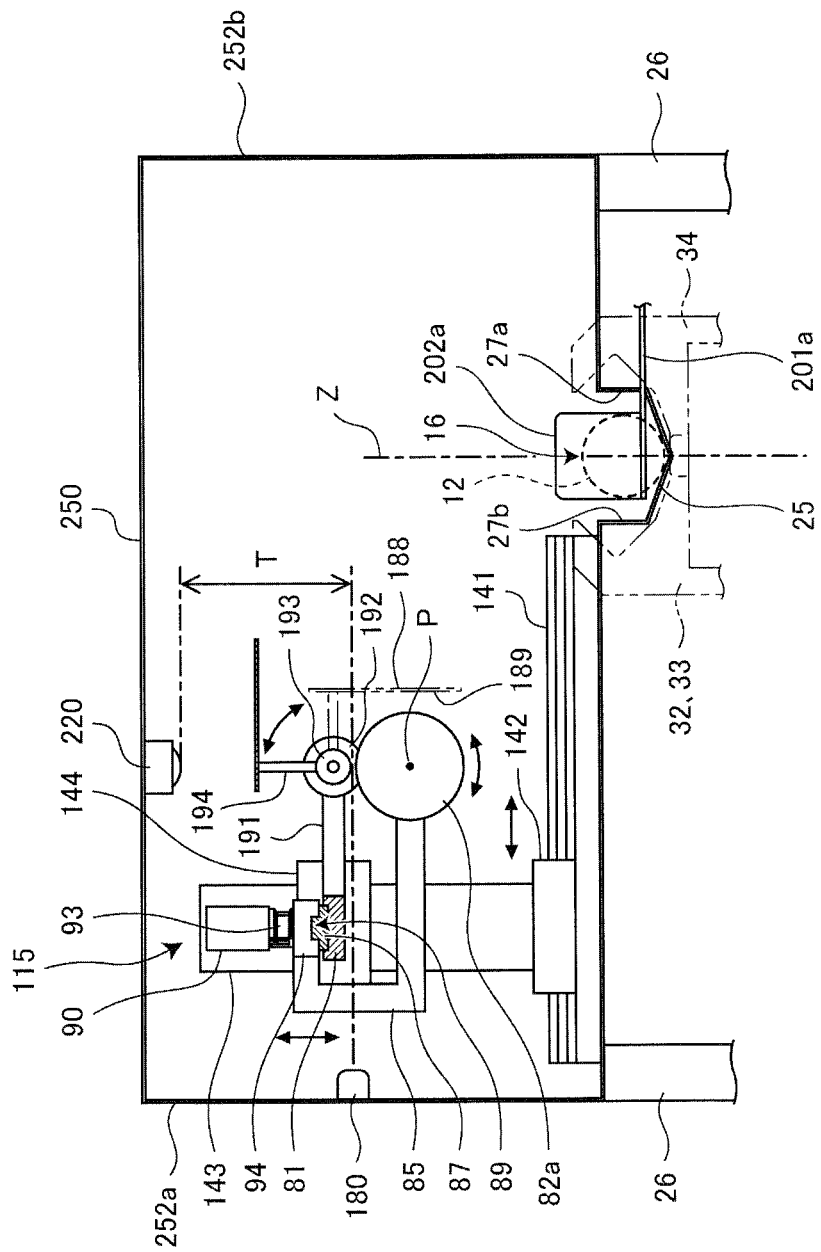
FIG. 3 is an explanatory view showing the section taken along the A-A line in FIG. 1.
Figure 4:
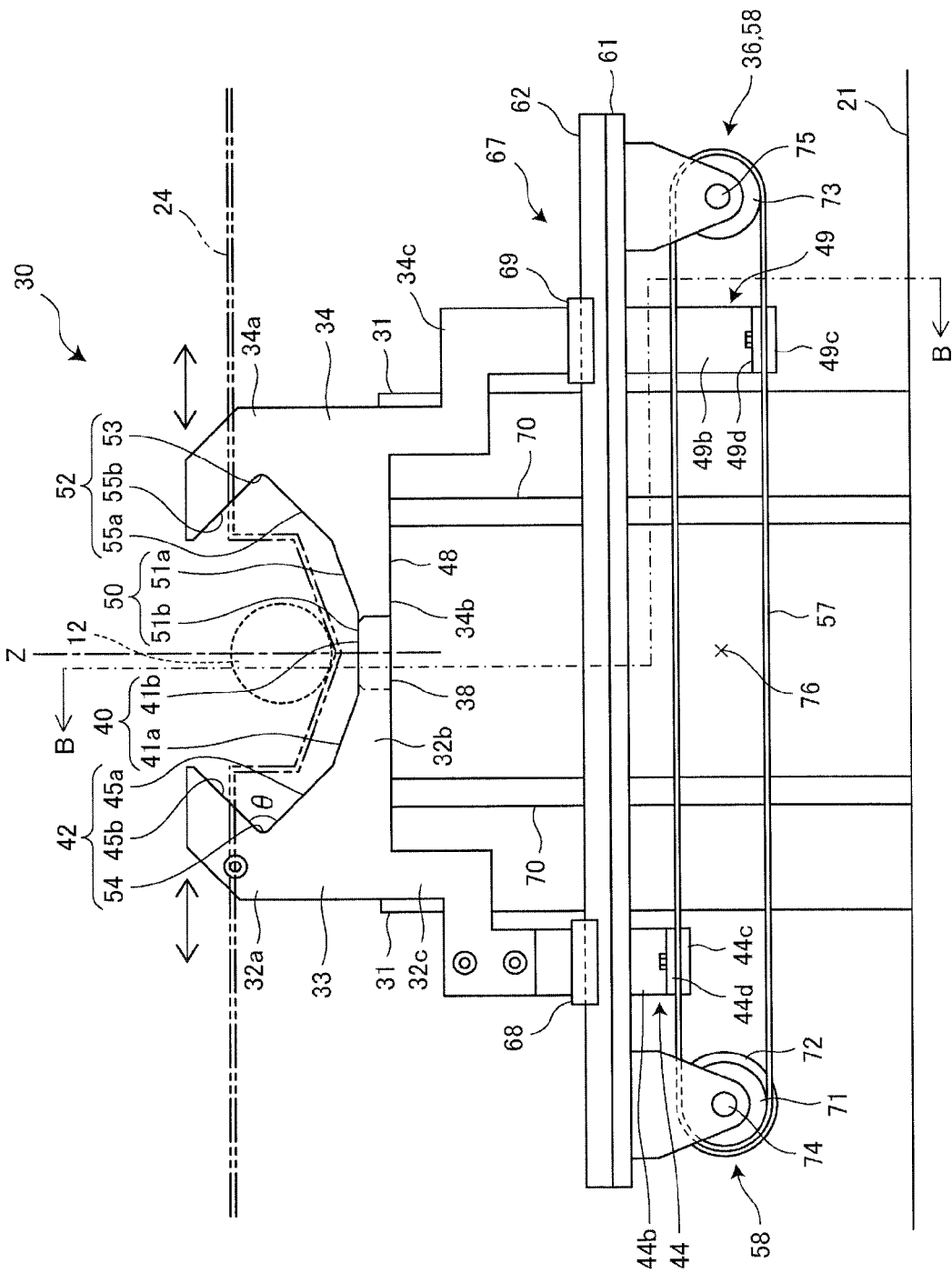
FIG. 4 is an explanatory view showing the front of a container clamping mechanism according to this embodiment.

FIG. 1 is an explanatory plan view of an information reader 10 of an injection container according to this embodiment and, more particularly, an explanatory plan view showing the state where a top plate 250 is removed therefrom. FIG. 2 is an explanatory view showing the right side surface of the information reader 10 of the injection container according to this embodiment, with a part thereof being omitted, FIG. 3 is an explanatory view showing the section taken along the A-A line in FIG. 1. FIG. 4 is an explanatory view showing the front of a container clamping mechanism according to this embodiment.

First, injection containers 9 and 12 shown in FIG. 1, FIG. 3, FIG. 4, FIG. 7 and FIG. 8 are containers used in medical settings such as hospitals in order to fill injections and the like, and include known ampules, vials, the so-called prefilled-type syringes in which the injections are filled in the syringes in advance and the like. Such containers are not limited to a cylindrical shape but may have various shapes including, for example, a hexagonal tubular shape having the cross section of an approximately hexagonal shape, a tubular shape having the cross section of a rectangular shape that is nearly oval and the like. Even when the cylindrical shapes are employed, they may have various diameters and the like, and may have different types of shapes and sizes.

The injection containers 9 and 12 include, for example, an empty container that is emptied after using the filled injection, and an unused container that contains the injection filled in the container, that has not been opened in an operation room or the like. The ampule may be emptied with its top being broken off. The prefilled-type syringe may be emptied in the state where a plunger for pressing out the injection in the syringe is pulled out, or in the state where the plunger is left inserted in the syringe. Thus, it is possible to assume that there are various states of the injection containers 9 and 12.

Each of the injection containers 9 and 12 has information attached on its outer periphery. More specifically, a label, for example, is attached on the outer peripheral surface of each of the injection containers 9 and 12, and the label includes, for example, characters showing a drug solution name, a date showing its shelf life and the like, and a bar code corresponding to the information. Such information may not be displayed on the label, but may be displayed by being printed on the outer peripheral surface of the injection containers 9 and 12.

Next, as shown in FIG. 1 and FIG. 2, the information reader 10 of the injection container according to this embodiment includes a base 20, a container supporting unit 14, a container clamping mechanism 30, a container rotation supporting mechanism 80, an imaging unit 220, a horizontal movement unit 140, a vertical movement unit 160, and laser distance measuring means 187.

First, as shown in FIG. 1 to FIG. 5, the base 20 is formed by a bottom plate 21 (refer to FIG. 4 and FIG. 5) that is formed by a plate member having, for example, a rectangular shape in a planar view, leg portions 26 (refer to FIG. 2) that are stood on the bottom plate 21, and a flat plate 24 (refer to FIG. 1 and FIG. 2) that is formed by a plate member having approximately the same shape and size as those of the bottom plate 21 and is horizontally supported by the leg portions 26.

Next, as shown in FIG. 1, the container supporting unit 14 of this embodiment includes a container inlet 16, a first supporting unit 22, and a second supporting unit 23.

As shown in FIG. 1 and FIG. 3, the container inlet 16 is an opening made in the flat plate 24, and has an elongated rectangular shape having long sides 29 and 29 about two times longer than, for example, the width of the palm of a person's hand, and a short side 15 about a half of the width of the palm of the hand. As shown in FIG. 1, the container inlet 16 is arranged near a predetermined side 19 of the flat plate 24, with its longitudinal direction being approximately parallel to the side 19. In FIG. 1, a center line M bisects the short side of the container inlet 16, and a center line N bisects the long side of the container inlet 16.

Hereinafter, the longitudinal direction of the container inlet 16 is referred to as an X direction, and the direction orthogonal thereto is referred to as a Y direction. In FIG. 2 and FIG. 3, side walls 252a and 252b are stood on respective sides of the flat plate 24 in the X direction, and the top plate 250 is provided on the top end of the side walls 252a and 252b.

As shown in FIG. 1, the container inlet 16 intersects an opening 16a that is made in the flat plate 24 in a thin rectangular shape. The opening 16a is formed to have the length about two or three times longer than the short side 15 of the container inlet 16 and the width about a half of the short side of the container inlet 16, for example. The opening 16a is arranged so that its center line bisecting its short side approximately overlaps with the center line N, and its center line bisecting its long side approximately overlaps with the center line M (refer to FIG. 1).

As shown in FIG. 1 and FIG. 3, the first supporting unit 22 is formed by a groove portion 25 that is in a V shape in a sectional view, that has, for example, approximately the same width as the short side 15 of the container supporting unit 14 and the length slightly shorter than about a half of the long side of the container inlet 16, and that extends in the X direction with such a depth to be able to receive the injection container 12, and wall plates 27a and 27b that are provided vertically from the upper sides of the groove portion 25 to the upward direction. As shown in FIG. 1 and FIG. 3, thus-formed first supporting unit 22 is arranged on one side of the center line N in the state where its center line in the direction of the groove, that is, the line along the lower end of the groove approximately corresponds to the center line M. The upper side portion of the wall plate 27a is connected to one long side 29 of the container inlet 16, and the upper side portion of the other wall plate 27b is connected to the other long side 29.

As shown in FIG. 1 and FIG. 3, the second supporting unit 23 is formed to have approximately the same shape and size as those of the first supporting unit 22. The second supporting unit 23 and the first supporting unit 22 are arranged to have line symmetry with respect to the center line N, while leaving space having the width of the opening 16a therebetween. Specifically, the container supporting unit 14 of this embodiment is formed in the flat plate 24 downwardly as a depression having the size of the container inlet 16, and has space 18 at the approximate center of its longitudinal direction. A pair of first clamping bodies 32 and 33 and a second clamping body 34 are arranged in the space 18, as will be described later.

As shown in FIG. 1 and FIG. 3, the injection container 12 introduced from the container inlet 16 is arranged approximately horizontally with its cylinder length direction corresponding to the X direction, and is supported from below by the container supporting unit 14.

Thus, according to this embodiment, the center line M forms the center line of the container supporting unit 14 in the cylinder length direction, whereas the center line N forms the container supporting unit center line N as the center line in the direction orthogonal to the cylinder length direction of the container supporting unit 14 (Y direction).

Next, the container clamping mechanism 30 as an essential part of this embodiment will be explained with reference to FIG. 1 and FIG. 4 to FIG. 6.

Figure 5:
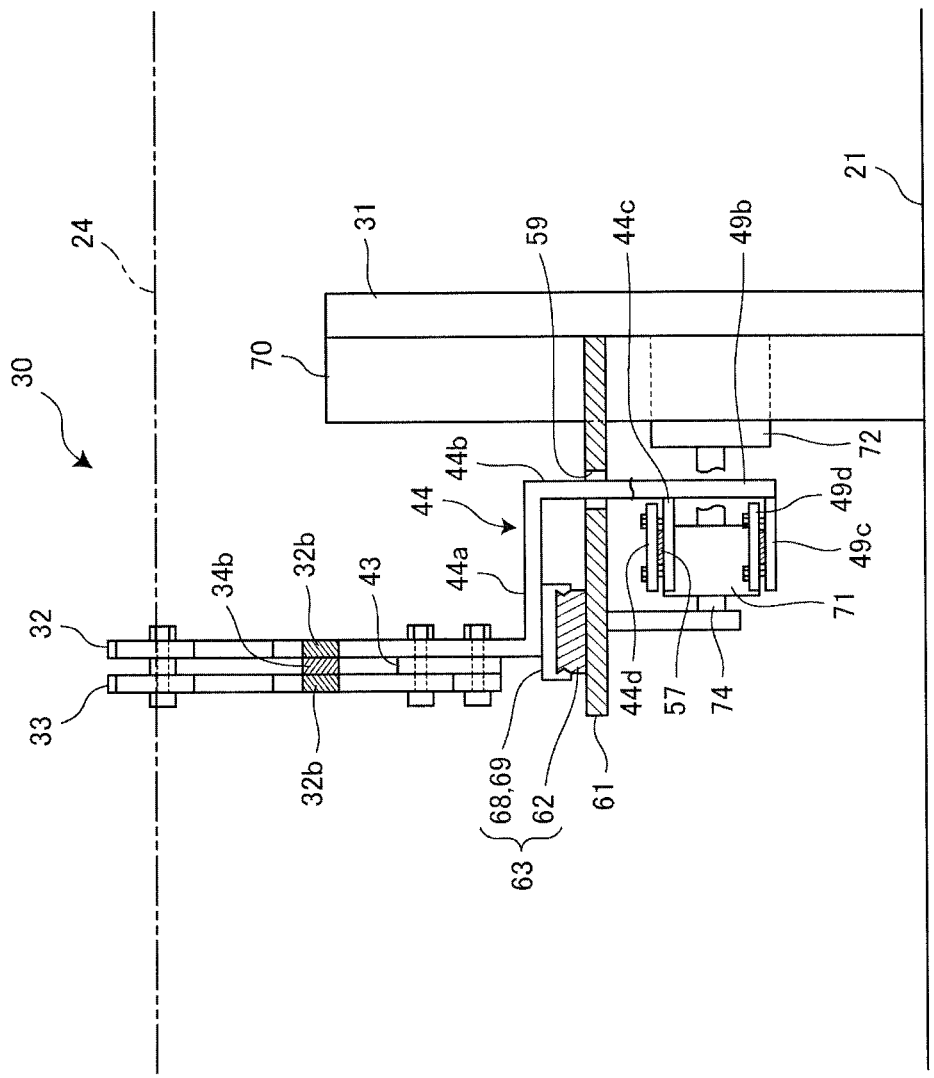
FIG. 5 is an explanatory view showing the section taken along the B-B line in FIG. 4.
Figure 6:
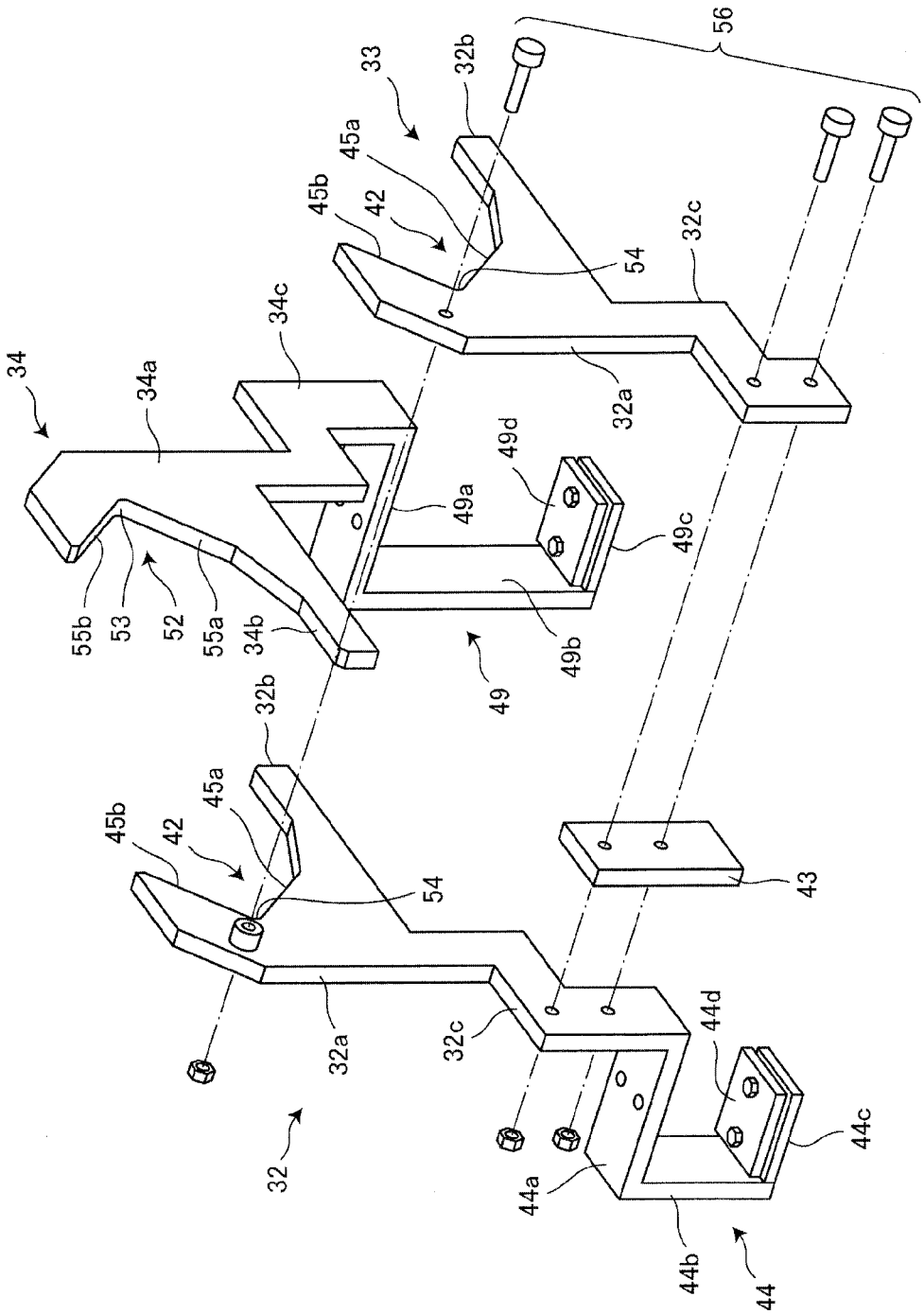
FIG. 6 is a perspective explanatory view of the container clamping mechanism according to this embodiment, with a part thereof being disassembled.

As shown in FIG. 4 to FIG. 6, the container clamping mechanism 30 includes a pair of the first clamping bodies 32 and 33, the second clamping body 34, a supporting unit 67 that supports the pair of the first clamping bodies 32 and 33 and the second clamping body 34 to be horizontally movable, and a driving mechanism 36.

As shown in FIG. 4 to FIG. 6, each of the first clamping bodies 32 and 33 of this embodiment is formed by, for example, one plate member, and includes a first clamping unit 32a, a first arm portion 32b, and a first leg portion 32c.

As shown in FIG. 4 to FIG. 6, the first clamping unit 32a is formed as the plate having a recess in a doglegged shape in one of two vertical sides opposing to each other, the recess including a first recess 42 having such a size to be able to receive the diameter of the injection container 9 in its recess. More specifically, as shown in FIG. 4, the first recess 42 includes an upper side 45b that extends with the angle of 45 degrees obliquely upward from a vertex 54 near the center of the first clamping unit 32a, and a lower side 45a that extends with the angle of 45 degrees obliquely downward from the vertex 54. According to this embodiment, a bend angle θ (refer to FIG. 5) of the first recess 42 is nearly at a right angle.

Next, as shown in FIG. 4 and FIG. 6, the first arm portion 32b is formed by a projection projecting approximately horizontally from the vicinity of the lower end of the first recess 42 in the direction opposite to the first recess 42. More specifically, the first arm portion 32b is formed as a laterally long plate, and includes an upper edge 40 formed by a slope side 41a that is a downslope gentler than the slope of the lower side 45 from the lower end of the first recess 42, and a horizontal side 41b that is approximately horizontal and is provided continuously with the slope side 41a. As shown in FIG. 4, a horizontal lower edge 38 of the first arm portion 32b extends from the lower end of the first clamping unit 32a, it should be noted that the first arm portion is not limited to the laterally long plate, and may have a rod shape.

As shown in FIG. 4 and FIG. 5, the first leg portion 32c is formed at the lower end portion of the first clamping unit 32a, and is formed to project from the vicinity a of the end opposite to the first arm portion 32b in the direction opposite to the first arm portion 32b and in a downward crank shape.

It should be noted that the difference between the first clamping body 33 and the first clamping body 32 is that the first clamping body 32 has a later-described first connecting unit 44, which will be described later.

The pair of the first clamping bodies 32 and 33 are arranged inside the above-described opening 16a, as shown in FIG. 1. Specifically, as shown in FIG. 1 and FIG. 3, the pair of the first clamping bodies 32 and 33 are arranged so that the respective plate surfaces are orthogonal to the X direction, and also arranged to face each other while leaving space therebetween, the space approximately corresponding to the plate thickness of the first clamping bodies 32 and 33. More specifically, as shown in FIG. 1, the first clamping body 33, as one of the pair of the first clamping bodies 32 and 33, is arranged in front of the container supporting unit center line N, for example, and the other first clamping body 32 is arranged at the position where the first clamping bodies 32 and 33 have line symmetry with respect to the container supporting unit center line N. At this time, the arrangement is made so that the first recesses 42 face toward the center line M.

As shown in FIG. 4 to FIG. 6, for example, the pair of the first clamping bodies 32 and 33 structured as above are connected via connecting means 56 such as screws, with a spacer plate 43 being inserted between the first leg portions 32c and 32c.

According to the structure of this embodiment, as shown in FIG. 4, each of the first clamping bodies 32 and 33 includes the recess in the approximate doglegged shape arranged on one side portion side of the injection container 12 supported by the container supporting unit 14, the recess being the first recess 42 that bends toward the direction allowing the vertex 54 to separate from the side portion when viewed from the cylinder length direction (X direction).

Further, according to the structure of this embodiment, the container clamping mechanism 30 includes the first clamping bodies arranged on one side portion side of the injection container 12, the first clamping bodies being the pair of the first clamping bodies 32 and 33 arranged to face each other while separating in the cylinder length direction.

As shown in FIG. 5 and FIG. 6, the first clamping body 32, out of the pair of the first clamping bodies 32 and 33, that is arranged behind the first clamping body 33, for example, has a first connecting unit 44 at its first leg portion 32c in order to connect to a horizontal slide piece 68 and an endless belt 57 that will be described later.

As shown in FIG. 5 and FIG. 6, the first connecting unit 44 includes, for example, a first upper horizontal plate 44a that projects horizontally backward from the first leg portion 32c, a first vertical plate 44b that is suspended from the back end of the first upper horizontal plate 44a, and a first lower horizontal plate 44c that is provided at the lower end of the first vertical plate 44b to oppose to the first upper horizontal plate 44a, which is formed in a substantially U shape as shown in FIG. 5. The first connecting unit 44 is connected and fixed to the lower end portion of the first leg portion 32c of the first clamping body 32. The connection between the first connecting unit 44 and the endless belt 57 will be described later.

As shown in FIG. 4 and FIG. 5, the first connecting unit 44 is arranged in such a manner that the later-described horizontal slide piece 68 is welded to the lower end surface of the first upper horizontal plate 44a, and the first vertical plate 44b passes through a slit 59 of a later-described ascending and descending plate body 61.

Next, the second clamping body 34 of this embodiment is formed to have the same shape and size as those of the first clamping bodies 32 and 33, as shown in FIG. 4 and FIG. 6. Specifically, the second clamping body 34 includes a second clamping unit 34a corresponding to the first clamping unit 32a, a second arm portion 34b corresponding to the first arm portion 32b, and a second leg portion 34c corresponding to the first leg portion 32c, as shown in FIG. 4 and FIG. 6.

In FIG. 4, a lower side 55a of a second recess 52, an upper side 55b of the second recess 52, and a vertex 53 of the second recess 52 are illustrated. Further, an upper edge 50 of a second arm portion 34b, a slope side 51a that is a downslope gentler than the slope of the lower side 55a from the lower end of the second recess 52, and a horizontal side 51b that is approximately horizontal and is provided continuously to the slope side 51a are illustrated. Furthermore, a lower edge of the second arm portion 34b and a lower end of a second clamping unit 34a continuing to the lower edge are illustrated as a reference numeral 48.

As shown in FIG. 1, FIG. 4 to FIG. 6, the second clamping body 34 is arranged to be inserted between the first clamping bodies 32 and 33 with its plate surface being approximately parallel to the plate surfaces of the first clamping bodies 32 and 33. More specifically, the second clamping body 34 is arranged so that the center of its plate thickness approximately corresponds to the container supporting unit center line N. Thus, the second clamping body 34 is arranged to be able to enter between the pair of the first clamping bodies 32 and 33. At this time, as shown in FIG. 4 and FIG. 6, the second clamping body 34 is arranged in such a manner that the second recess 52 faces toward the center line M and the height of the position of the vertex 53 is approximately level with the position of the vertexes 54 of the first recesses 42.

As shown in FIG. 1, FIG. 2 and FIG. 4, the first recesses 42 and the second recess 52 are arranged to have line symmetry with respect to a center line Z that vertically passes through the intersection between the above-described center line M and the center line N, when viewed from the X direction.

According to the structure of this embodiment, as shown in FIG. 4, the second clamping body 34 includes the second clamping unit 34a having the second recess 52 that is formed to face against the first recesses 42 and has an approximately reverse doglegged shape. It should be noted that the pair of the first clamping bodies 32 and 33 and the second clamping body 34 are arranged to have the line symmetry with respect to the above-described center line Z, as shown in FIG. 4.

Similarly to the first clamping body 32, the second clamping body 34 has a second connecting unit 49 at its lower end portion in order to connect to the horizontal slide piece 69 and the endless belt 57 that will be described later. The difference between the second connecting unit 49 and the first connecting unit 44 is that the length of a second vertical plate 49b is greater than the length of the first vertical plate 44b of the first connecting unit 44, as shown in FIG. 4 to FIG. 6. More specifically, as shown in FIG. 6, the second connecting unit 49 includes a second upper horizontal plate 49a corresponding to the first upper horizontal plate 44a, a second lower horizontal plate 49c corresponding to the first lower horizontal plate 44c, and the second vertical plate 49b that is longer than the first vertical plate 44b.

As shown in FIG. 4 and FIG. 5, the second connecting unit 49 is arranged in such a manner that the later-described horizontal slide piece 69 is welded to the lower end surface of the second upper horizontal plate 49a, and the second vertical plate 49b passes through the later-described slit 59.

Next, as shown in FIG. 4 and FIG. 5, the supporting unit 67 of this embodiment includes a wall body 31, the ascending and descending plate body 61, and horizontal movement means 63.

As shown in FIG. 4 and FIG. 5, the wall body 31 of this embodiment is formed by a plate member in an approximate square shape whose one side corresponds to the length of the opening 16a in the Y direction, for example. The wall body 31 is stood on the bottom plate 21 under the vicinity of the opening 16a, with its plate surface being parallel to the Y direction. Further, as shown in FIG. 4 and FIG. 5, the wall body 31 includes two vertical rails 70 on its wall surface on the front side, in order to guide ascent and descent of the later-described ascending and descending plate body 61.

Next, as shown in FIG. 4 and FIG. 5, the ascending and descending plate body 61 is formed by a rectangular-shaped plate member whose long side is, for example, about two times longer than the length of the opening 16a in the Y direction, and is slidably connected to the vertical rails 70 with its long side corresponding to the V direction and its plate surface being horizontal. The ascending and descending plate body 61 is also structured to ascend and descend along the vertical rails 70 by, for example, a known ascending and descending mechanism including long screws (not shown) vertically provided along the vertical rails 70 and female threads (not shown) screwing into the long screws. Further, as shown in FIG. 5, the slit 59 along the longitudinal direction of the ascending and descending plate body 61 is formed at the center of the ascending and descending plate body 61. The slit 59 is an opening for preventing the first clamping body 32 and the second clamping body 34 from being interrupted during movement.

Next, as shown in FIG. 5, the horizontal movement means 63 includes a slide rail 62 and the horizontal slide pieces 68 and 69.

The slide rail 62 of this embodiment is formed by, for example, a known LM rail and is fixedly provided on the ascending and descending plate body 61 in front of the slit 59, with its longitudinal direction corresponding to the Y direction, as shown in FIG. 4 and FIG. 5.

Further, each of the horizontal slide pieces 68 and 69 is formed by, for example, a known LM block, and is structured to be slidable along the slide rail 62, as shown in FIG. 4 and FIG. 5.

Next, the driving mechanism 36 includes the endless belt 57 formed by a known revolving belt, and rotating means 58 that rotates the endless belt 57, as shown in FIG. 4 and FIG. 5.

The rotating means 58 includes a roller 71, a motor 72, and a pulley 73.

First, the motor 72 is formed by for example, a known stepping motor, and rotates the roller 71 about a rotation axis 74 that is kept horizontally, as shown in FIG. 4 and FIG. 5. The motor 72 is arranged under one end side of the ascending and descending plate body 61, and held by the ascending and descending plate body 61 in a suspended manner, as shown in FIG. 4 and FIG. 5.

The pulley 73 is rotatably supported around a rotation axis 75 that is horizontal and arranged under the other end side of the ascending and descending plate body 61, and held by the ascending and descending plate body 61 in a suspended manner. The endless belt 57 is suspended between the roller 71 and the pulley 73 and is rotated in a vertical plane. It should be noted that a mark "x" shown by a reference numeral 76 in FIG. 4 shows the center of the rotation of the endless belt 57.

Next, the connection between the endless belt 57 and the above-described first clamping body 32 and the second clamping body 34 will be explained.

When the first clamping body 32 of this embodiment is connected to the horizontal slide piece 68 in the manner described above, it is arranged at the height allowing, for example, the portion of the endless belt 57 higher than the above-described center of the rotation 76 to be carried on the top surface of the first lower horizontal plate 44c, as shown in FIG. 4 and FIG. 5. Then, the endless belt 57 is disposed between a plate-shaped first clamping plate piece 44d that is connected to the first lower horizontal plate 44c by screws and the like and the first lower horizontal plate 44*c*, so that the first clamping body 32 and the endless belt 57 are connected.

Next, when the second clamping body 34 of this embodiment is connected to the horizontal slide piece 69 in the manner described above, it is arranged at the height allowing the portion of the endless belt 57 lower than the center of the rotation 76 to be carried on the top surface of the second lower horizontal plate 49*c*, as shown in FIG. 4 and FIG. 5. Then, the endless belt 57 is disposed between a plate-shaped second clamping plate piece 49*d* that is connected to the second lower horizontal plate 49*c* by screws and the like and the second lower horizontal plate 49*c*, so that the second clamping body 34 and the endless belt 57 are connected.

According to the structure described above, when the endless belt 57 is rotated by the motor 72, the pair of the first clamping bodies 32 and 33 simultaneously advance or retreat in the horizontal direction that is almost orthogonal to the cylindrical length direction, and at the same time, the second clamping body 34 advances or retreats in the direction opposite to the advancing or retreating direction of the first clamping bodies 32 and 33. As the second clamping body 34 is arranged in such a manner that the center of its plate thickness approximately corresponds to the container supporting unit center line N, as described above, it advances or retreats approximately along the container supporting unit center line N.

Therefore, according to the structure of this embodiment, the container clamping mechanism 30 includes the driving mechanism 36 provided to allow the pair of the first clamping bodies 32 and 33 to simultaneously advance or retreat in the horizontal direction that is almost orthogonal to the cylinder length direction (Y direction), and at the same time, allow the second clamping body 34 to advance or retreat in the direction opposite to the advancing or retreating direction.

It should be noted that the container clamping mechanism 30 of this embodiment is provided with motor control means (not shown) such as, for example, a known overload sensor, CPU and the like. It is structured to be able to control the force for clamping the injection containers 9 and 12 by controlling torque of the motor 72, so as to prevent the injection containers from being deformed or damaged.

Next, the container rotation supporting mechanism 80 will be explained by mainly referring to FIG. 1 to FIG. 3.

As shown in FIG. 1, the container rotation supporting mechanism 80 of this embodiment includes an elongated plate 81, a pair of clamping pads 82*a* and 82*b*, a first supporting arm 86, a second supporting arm 85, approaching and separating movement means 83, a rotating unit 84, a pivoting unit 113, a reflector plate 188, a reflector plate rotating mechanism 190 and the like.

The elongated plate 81 is formed by a plate having, for example, the length about 1.2 times greater than the length of the container supporting unit 14, and the width about a half of the width of the container supporting unit 14, as shown in FIG. 1 and FIG. 2. The elongated plate 81 is arranged to face against the container supporting unit 14 in the state where its plate surface is made approximately horizontal and its longitudinal direction is made approximately parallel to the longitudinal direction of the container supporting unit 14 (X direction), as shown in FIG. 1 and FIG. 2. One end side of the elongated plate 81 in the longitudinal direction is supported by a later-described ascending and descending body 144 in a cantilever state.

Next, each of the pair of the clamping pads 82*a* and 82*b* is, for example, formed by a circular plate having the diameter corresponding to the approximate width of the container supporting unit 14, as shown in FIG. 1 and FIG. 3. As shown in FIG. 1 to FIG. 3, the pair of the clamping pads 82*a* and 82*b* are arranged to face each other, with plate surfaces thereof being almost parallel to the Y direction, at the position slightly lower than the position that is horizontally spaced from the side portion of the elongated plate 81 on the container supporting unit 14 side by the approximate width of for example, the container supporting unit 14. At this time, as shown in FIG. 1, the pair of the clamping pads 82*a* and 82*b* are arranged to have approximate line symmetry with respect to the container supporting unit center line N. The clamping pad 82*a* is rotatably supported by the later-described rotating unit 84, whereas the clamping pad 82*b* is rotatably supported by the later-described first supporting arm 86.

Thus, according to the structure of this embodiment, the container rotation supporting mechanism 80 includes the pair of the clamping pads 82*a* and 82*b* that are opposed to each other at the position slightly separated from one side portion of the elongated plate 81.

Next, the rotating unit 84 can be structured by a known stepping motor and, as shown in FIG. 1 and FIG. 2, is supported by the later-described second supporting arm 85 with its rotation axis P approximately corresponding to the X direction. In FIG. 1 and FIG. 2, a rotating rod 103 of the rotating unit 84 is illustrated. The clamping pad 82*a* is rotatably supported by the rotating rod 103 so that its center of rotation corresponds to the rotation axis P, as shown in FIG. 1 and FIG. 2.

Next, the approaching and separating movement means 83 includes an endless belt 91, rotating means 115 to rotate the endless belt 91, a guide member 87, a pair of slide bodies 88*a* and 88*b* and the like, as shown in FIG. 1 and FIG. 2.

The rotating means 115 includes a roller 93, a motor 90, and a pulley 92, as shown in FIG. 1 and FIG. 2. The motor 90 may be formed by, for example, a known stepping motor, and rotates the roller 93 about an approximately vertical rotation axis K. Then the motor 90 and the roller 93 are provided on one side of the top surface of the elongated plate 81, as shown in FIG. 1 and FIG. 2. In FIG. 1 and FIG. 2, a bearing 116 such as a ball bearing is illustrated, and the rotation axis K is rotatably supported by the bearing 116.

As shown in FIG. 1 and FIG. 2, the pulley 92 has an approximately vertical rotation axis L, and is rotatably supported by a bearing provided on the other side of the top surface of the elongated plate 81. Then, the endless belt 91 is suspended between the roller 93 and the pulley 92 for rotation.

The guide member 87 is formed by, for example, a rail that is convex in a sectional view and has the width slightly narrower than that of the elongated plate 81 and the length about three-quarters of that of the elongated plate 81, as shown in FIG. 1 to FIG. 3. The guide member 87 is fixedly provided on the to surface of the elongated plate 81 by, for example, being embedded therein (refer to FIG. 3), with its longitudinal direction corresponding to the longitudinal direction of the elongated plate 81, as shown in FIG. 1 to FIG. 3.

Each of the slide bodies 88*a* and 88*b* is formed by a block 94 that has an approximately square shape and has the side length approximately corresponding to, for example, the width of the elongated plate 81, and a pair of clamping pieces 95 and 95 stood thereon, as shown in FIG. 1 and FIG. 2. The slide bodies 88*a* and 88*b* are structured to freely slide along the guide member 87 as a groove portion 89 that is formed concavely in the block 94 (refer to FIG. 3) fits with the guide member 87.

Specifically, the slide body 88*a* is arranged on the guide member 87 near the pulley 92, for example, and connected to the endless belt 91, as shown in FIG. 1 and FIG. 2. At this time, as shown in FIG. 1, the slide body 88a clamps between the pair of the clamping pieces 95 and 95 the belt portion of the endless belt 91 that is located on one side of the line (not shown) connecting the rotation axis K and the rotation axis L, and is connected to the endless belt 91 by, for example, screws 96.

Meanwhile, the slide body 88b is arranged on the guide member 87 near the roller 93, for example, and connected to the endless belt 91, as shown in FIG. 1 and FIG. 2. At this time, as shown in FIG. 1, the slide body 88b is connected to the belt portion of the endless belt 91 that is located on the other side of the line connecting the rotation axis K and the rotation axis L in the manner similar to the above.

Thus, when the endless belt 91 rotates in response to the motor 90, the pair of the slide bodies 88a and 88b that are opposed to each other move approachingly and separatingly at the same speed in the longitudinal direction of the elongated plate 81 (X direction).

Next, the first supporting arm 86 is formed by a vertical rod 97 that has, for example, the length approximately the same as the width of the elongated plate 81, and a linear rod 99 that has the length approximately the same as the width of the container supporting unit 14 and is provided horizontally from the lower end of the vertical rod 97 in a protruding manner, as shown in FIG. 1 and FIG. 2. With the first supporting arm 86, the upper end portion of the vertical rod 97 is fixedly provided to the side portion of the slide body 88a on the side where the clamping pad 82b is arranged, and the tip end portion of the rod 99 supports the later-described pivoting unit 113, as shown in FIG. 1 and FIG. 2.

Next, the pivoting unit 113 is formed by a bearing unit 113a such as a ball bearing, a rotating rod 113b that is rotatably supported by the bearing unit 113a, and the like, as shown in FIG. 1 and FIG. 2. The rotating rod 113b is arranged in such a manner that its rotation axis corresponds to the above-described rotation axis P, and pivotally and rotatably supports the clamping pad 8211 in other words, the clamping pad 82b is rotatably supported about the rotation axis P.

Next, as shown in FIG. 2 and FIG. 3, the second supporting arm 85 is formed by the rod bent in a substantially U shape, and arranged so that it is substantially U-shaped when viewed from the X direction. More specifically, as shown in FIG. 3, the tip portion of the upper side of the U-shaped second supporting arm 85 is fixedly provided to the side portion of the slide body 88b that is on the side opposite to the side where the clamping pad 82b is arranged, and the tip portion of the lower side of the U shape passes through the space near and under the rear surface of the elongated plate 81, and projects from the side portion of the elongated plate 81 that is on the side where the clamping pad 82b is arranged. Then, as shown in FIG. 1, the second supporting arm 85 supports the rotating unit 84 arranged as above.

Thus, the pair of the clamping pads 82a and 82b of this embodiment move approachingly and separatingly via the slide bodies 88a and 88b, while maintaining the line symmetry with respect to the container supporting unit center line N as the center line. Therefore, when the injection container 12 is arranged between the pair of the clamping pads 82a and 82b with its cylinder length direction corresponding to the X direction, the both end portions of the injection container 12 can be clamped when the pair of the clamping pads 82a and 82b approach each other.

It should be noted that the motor 90 is provided with control means such as, for example, a known overload sensor, CPU and the like, and the rotation of the motor 90 is stopped according to the force applied in the cylinder length direction at the time when the pair of the clamping pads 82a and 82b clamp the both end portions of the injection container 12. Consequently, it is possible for the container rotation supporting mechanism 80 to clamp the injection container 12 by the appropriate force so as not to deform the injection container 12.

The approaching and separating movement means 83 of this embodiment uses the rotation of the endless belt 91 as described above, but the approaching and separating movement means is not limited thereto, and, for example, a known LM guide mechanism may be used. For example, a pair of LM blocks are arranged on an LM rail, and the LM blocks are moved approachingly and separatingly on the LM rail.

Next, the reflector plate 188 is formed by a rectangular thin plate having long sides whose length is, for example, about two-thirds of the length of the elongated plate 81 and short sides whose length is about the same as the width of the container supporting unit 14, as shown in FIG. 1 to FIG. 3. At least either one of the plate surfaces forms a reflection plane 189 to reflect laser light (as will be described later). The reflector plate 188 is supported by a later-described reflector plate supporting rod 194 with its longitudinal direction corresponding to the X direction.

Next, the reflector plate rotating mechanism 190 includes a motor 192, a rotor 193, and the reflector plate supporting rod 194, as shown in FIG. 1 to FIG. 3.

First, as shown in FIG. 2, the motor 192 is arranged at the position near and over the above-described rotating unit 84, with its rotation axis F being approximately parallel to the rotation axis P, and is supported by a later-described supporting plate 191.

Next, as shown in FIG. 1 and FIG. 3, the rotor 193 is formed by a circular plate having the diameter of, for example, about one-third of the radius of the clamping pads 82a and 82b. The rotor 193 is pivotally supported by the motor 192 to be rotatable about the rotation axis F, with its plate surface being approximately parallel to the Y direction.

Next, as shown in FIG. 1 and FIG. 3, the supporting plate 191 is formed by, for example, a thin rectangular plate, and is fixedly provided at the side portion of the elongated plate 81 in such a manner to project horizontally from the side portion of the elongated plate 81. Then, the supporting plate 191 supports the motor 192 arranged as above.

Next, as shown in FIG. 2 and FIG. 3, the reflector plate supporting rod 194 is formed by a rod whose length approximately corresponds to the radius of the clamping pads 82a and 82b, for example, and provided to the outer periphery of the rotor 193 in a protruding manner with its longitudinal direction being orthogonal to the rotation axis F. As shown in FIG. 1 to FIG. 3, the reflector plate supporting rod 194 has the above-described reflector plate 188 fixed at its tip side. Here, the reflection plane 189 side of the reflector plate 188 is connected to the reflector plate supporting rod 194 at one end side of the reflector plate 188 in the longitudinal direction, as shown in FIG. 1 to FIG. 3.

Thus, as shown in FIG. 3, the reflector plate 188 can rotate in response to the rotation of the motor 192 while allowing the reflection plane 189 to face toward the rotation axis F, so as to locate the plate surface of the reflector plate 188 horizontally, or locate the reflection plane 189 approximately vertically.

Next, the horizontal movement unit 140 includes a guide rail 141 and a horizontal slide body 142 as shown in FIG. 1 to FIG. 3.

The guide rail 141 is formed by, for example, a known LM rail. From a base end that is near one end side of the container supporting unit 14, it extends approximately horizontally in the Y direction.

The horizontal slide body 142 is formed by, for example, a known LM block, and is structured slidably along the guide rail 141.

Next, the vertical movement unit 160 includes a vertical rail 143 and an ascending and descending body 144, as shown in FIG. 2.

The vertical rail 143 may be formed by, for example, a known LM rail. Specifically, the vertical rail 143 is formed by, for example, the LM rail having the length approximately the same as that of the guide rail 141, as shown in FIG. 2 and FIG. 3, and is fixedly provided to the horizontal slide body 142 with its longitudinal direction being approximately vertical.

The ascending and descending body 144 may be formed by, for example, a known LM block. Specifically, the ascending and descending body 144 is formed by the LM block having the size capable of supporting the above-described elongated plate 81, for example, and connected to the side portion of the vertical rail 143 to be able to ascend/descend along its longitudinal direction.

Thus, according to the structure of this embodiment, the information reader 10 of the injection container includes the vertical movement unit 160 that allows the container rotation supporting mechanism 80 to move approximately vertically, and the horizontal movement unit 140 that allows the vertical movement unit 160 to move approximately horizontally, as the elongated plate 81 is supported by the ascending and descending body 144 as described above.

Next, the imaging unit 220 is formed by, for example, a known digital camera. As shown in FIG. 1 and FIG. 3, the imaging unit 220 is fixedly provided to the above-described top plate above the position that is separated from the container supporting unit 14 by a distance about a half of the length of the guide rail 141 along the container supporting unit center line N, for example. Therefore, as shown in FIG. 3, the container rotation supporting mechanism 80 can be moved by the horizontal movement unit 140, while clamping the injection container 12, and the injection container 12 can be arranged at the position under the imaging unit 220.

Thus, it is possible for the imaging unit 220 to capture an image of the outer peripheral surface of the injection container 12 clamped by the container rotation supporting mechanism 80.

It should be noted that the imaging unit 220 is set to focus on a subject arranged at the position separated from the imaging unit 220 by a predetermined distance, as shown in FIG. 3. Hereinafter, the predetermined distance is referred to as a subject distance T.

It should be noted that the information reader 10 of the injection container according to this embodiment includes information recognizing means that recognizes the information on the label attached on the outer peripheral surface of the injection container 12, based on the image data from the imaging unit 220. The information recognizing means may employ, for example, known OCR (Optical Character Recognition) technology, pattern matching technique to read the information on the label by pattern matching between the image data that is stored in advance and the image data that is read from the label, a bar code reader, and the like.

Next, as shown in FIG. 1, the laser distance measuring means 187 includes a laser light projecting unit 180, a light receiving unit 181, a timer (not shown), a CPU (not shown), memory (not shown) and the like.

First, the laser light projecting unit 180 includes, for example, a known pulse generator and the like, and can be formed by a pulsed laser projector to project pulsed laser light. As shown in FIG. 3, the laser light projecting unit 180 is fixedly provided to the side wall 252a, and projects the laser light approximately horizontally passing through the position that is under the imaging unit 220 and is separated therefrom by the subject distance T.

Thus, according to the structure of this embodiment, the laser distance measuring means 187 includes the laser light projecting unit 180 for projecting the pulsed laser light horizontally passing through the position that is under the imaging unit 220 and is at the predetermined height.

Next, the light receiving unit 181 may be formed by, for example, a known laser light detector, and transmits a light reception signal when it receives the laser light. As shown in FIG. 1 and FIG. 3, the light receiving unit 181 is fixedly provided on the side wall 252a at the position that is next to and as almost the same height as the laser light projecting unit 180, and is arranged to be able to receive the reflected light of the laser light projected from the laser light projecting unit 180. It should be noted that, in FIG. 1, the laser light Q is projected from the laser light projecting unit 180, and the reflected light E is reflected from the reflector plate 188.

Further, the timer includes, for example, a counter circuit, and transmits time data from the projection of the pulsed laser by the laser light projecting unit 180 until the reception of the light reception signal to the CPU. When receiving the time data, the CPU calculates the distance to the target based on the time data.

Thus, according to the structure of this embodiment, the information reader 10 of the injection container includes the laser distance measuring means 187 that measures the distance to the target based on the time from the projection of the laser light toward the target until the reception of the reflected light from the target.

It should be noted that the CPU and the memory function as ascending and descending means that allows the container rotation supporting mechanism 80 to ascend and descend. For example, a reference distance is stored in the memory in advance and, when the distance to the target measured by the laser distance measuring means 187 is substantially the same as the reference distance, the CPU gives an instruction to the vertical movement unit 160 so as to move the container rotation supporting mechanism 80 upward, and when the distance to the target is shorter than the reference distance, the CPU gives an instruction to the vertical movement unit 160 so as to stop the upward movement of the container rotation supporting mechanism 80.

Thus, according to the structure of this embodiment, it is possible for the vertical movement unit 160 to allow the container rotation supporting mechanism to move upward and downward based on the distance to the target measured by the laser distance measuring means 187, via the CPU and the memory.

Further, the information reader 10 of the injection container according to this embodiment includes container centering means 200, as shown in FIG. 1 to FIG. 3.

The container centering means 200 includes a pair of centering pads 202a and 202b, and approaching and separating movement means (not shown) for moving the centering pad 202a and the centering pad 202b approachingly and separatingly. As the structure of the approaching and separating movement means is similar to that of the above-described approaching and separating movement means 83, detailed explanations thereof are omitted.

Therefore, even when the injection container 12 is supported in the state where its container center line R (refer to FIG. 7A) bisecting its length in the cylinder length direction does not correspond to the container supporting unit center line N, the injection container 12 that is arranged between the pair of the centering pads 202a and 202b may be moved in the longitudinal direction (X direction) of the container supporting unit 14 when the pair of the centering pads 202a and 202b approach, so that the container center line R approximately corresponds to the container supporting unit center line N.

An operation example of thus-structured information reader 10 of the injection container according to this embodiment will be explained with reference to the drawings. FIG. 7 to FIG. 10 are explanatory views schematically showing the operation example of the information reader 10 of the injection container. In FIG. 7 to FIG. 10, arrows S1 to S13 show directions of movement and rotation of the respective components.

Figure 7A:
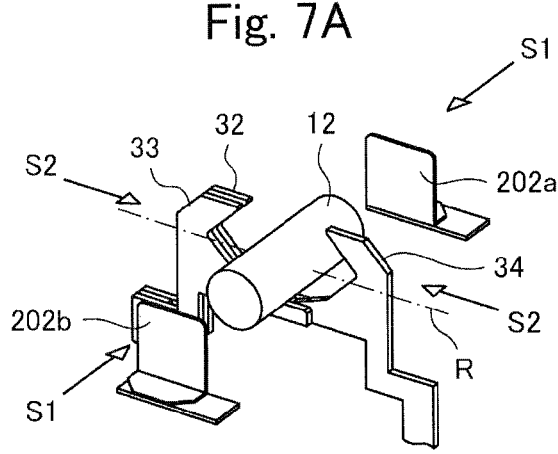
FIGS. 7A, 7B and 7C are explanatory views schematically showing an operation example of the information reader of the injection container according to this embodiment.

First, as shown in FIG. 7A, the injection container 12 is supported by the container supporting unit 14. Then, the pair of the centering pads 202a and 202b that oppose each other approach each other (arrows S1) to allow the injection container 12 to move, so that the container center line R corresponds to the container supporting unit center line N.

Figure 7B:
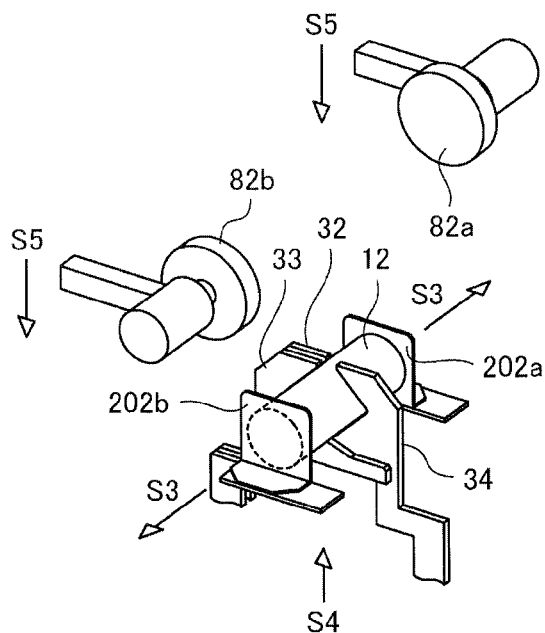

Next, as shown in FIG. 7A, the pair of the first clamping bodies 32 and 33 and the second clamping body 34 that oppose each other approach each other (arrows S2) and clamp the side portions of the injection container 12 (refer to FIG. 7B).

Now, the clamping of the side portions of the injection container 12 by the pair of the first clamping bodies 32 and 33 and the second clamping body 34 will be explained in detail with reference to the example in FIG. 10. FIG. 10 are views explaining the operation viewed from the front side. FIG. 10 shows the injection container 9 having the cross section of, for example, an approximately square shape, the center 11 of the line connecting the above-described vertexes 54 of the first recesses 42 and the vertex 53 of the second recess 52, that is, the intersection between the line connecting the vertexes 54 and the vertex 53 and the above-described center line Z, and a central axis 13 of the injection container 9 in the cylinder length direction.

Figure 10A:
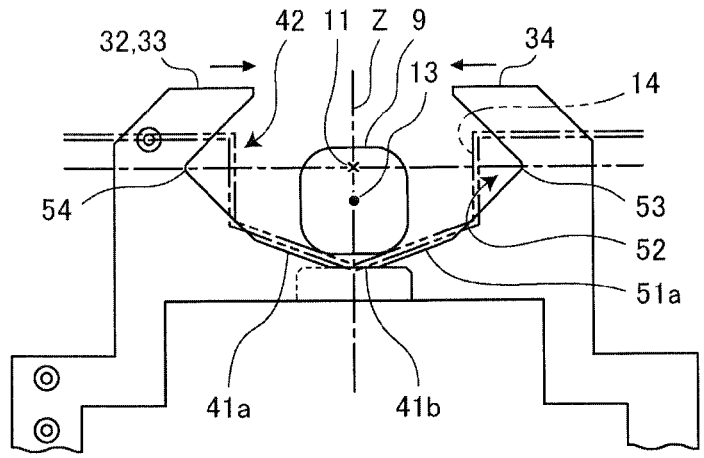
FIGS. 10A, 10B and 10C are explanatory views schematically showing the operation examples of the information reader of the injection container according to this embodiment.

First, FIG. 10A shows the state in which the injection container 9 is supported by the container supporting unit 14. When the pair of the first clamping bodies 32 and 33 and the second clamping body 34 approach from this state, the slope sides 41a of the first clamping bodies 32 and 33 and the slope side 51a of the second clamping body 34 support the injection container 9 from below, instead of the container supporting unit 14, and the injection container 9 gradually moves upward along the slope sides 41a and 51a.

Figure 10B:
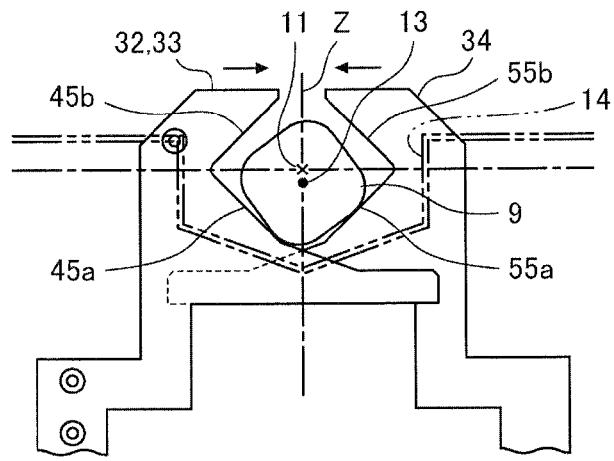

Next, as shown in FIG. 10B, when the pair of the first clamping bodies 32 and 33 and the second clamping body 34 approach further, the injection container 9 moves further upward while being supported by the lower sides 45a of the first recesses 42 and the lower side 55a of the second recess 52. At this time, the lower side 55a and the lower sides 45a approach while facing each other, that is, while maintaining approximate line symmetry with respect to the center line Z. Therefore, the injection container 9 is moved upward while being located at the center, with its central axis 13 being positioned under the center 11.

Figure 10C:
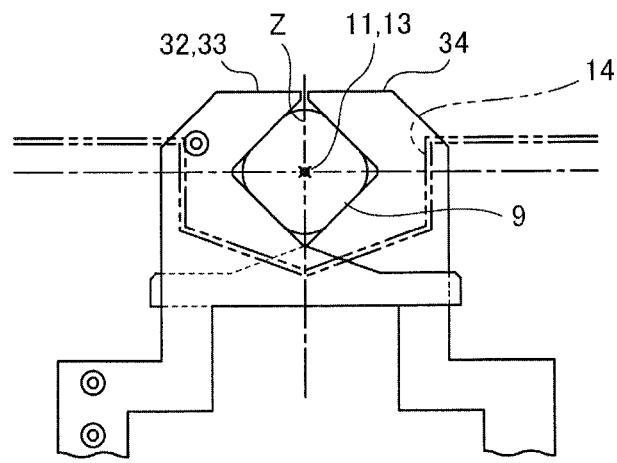

The pair of the first clamping bodies 32 and 33 and the second clamping body 34 approach further and, when the central axis 13 in the cylinder length direction corresponds to the above-described center 11, as shown in FIG. 10C, the upper end portion of the injection container 9 abuts against the upper sides 45b of the first recesses 42 and the upper side 55b of the second recess 52, so that the upward movement of the injection container 9 is limited.

Thus, the container clamping mechanism 30 allows the pair of the first recesses 42 and the second recess 52 substantially facing each other to move approachingly and separatingly by the driving mechanism 36, and clamps the injection containers 12 and 9 in the state where the central axis 13 in the cylinder length direction approximately intersects the center 11 of the line connecting the vertexes 54 of the first recesses 42 and the vertex 53 of the second recess 52 at the time of approaching.

Therefore, according to the structure of this embodiment, the information reader 10 of the injection container includes the container clamping mechanism for removably clamping the side portions of the injection container whose cylinder length direction is made approximately horizontal.

At this time, as the second clamping body 34 advances or retreats along the container supporting unit center line N, as described above, it is possible to clamp the approximate center of the injection container 12 in the cylinder length direction.

Although the explanations are made about the case where the injection container 9 has the approximately square cross-sectional shape, the cross-sectional shape may be circular or oval.

Next, as shown in FIG. 7B, the pair of the centering pads 202a and 202b separate from the both ends of the injection container 12 (arrows S3). Then, as shown in FIG. 7B, the ascending and descending plate body 61 is moved upward by the above-described ascending and descending mechanism, so that the pair of the first clamping bodies 32 and 33 and the second clamping body 34 are moved upward to the predetermined height while clamping the side portions of the injection container 12 (arrow S4).

Next, as shown in FIG. 7B, the pair of the clamping pads 82a and 82b are moved horizontally by the horizontal movement unit 140 so that its rotation axis P is located above the central axis 13 of the injection container 12. Then, the pair of the clamping pads 82a and 82b are moved downward by the vertical movement unit 160 (arrows S5), until the rotation axis P approximately corresponds to the central axis 13.

Figure 7C:
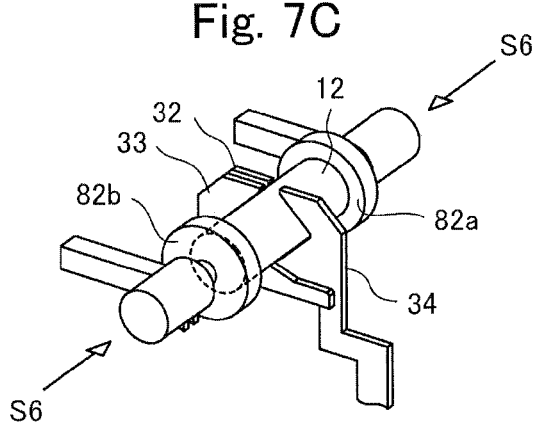

Next, as shown in FIG. 7C, the pair of the clamping pads 82a and 82b that are opposed to each other approach each other (arrows S6), and clamp the both end portions of the injection container 12 therebetween.

In order to prevent the pair of the clamping pads 82a and 82b from being interrupted when clamping the injection container 12 therebetween, the above-described reflector plate 188 is rotated by the reflector plate rotating mechanism 190 so that its plate surface is arranged to be approximately horizontal (refer to FIG. 3).

Figure 8A:
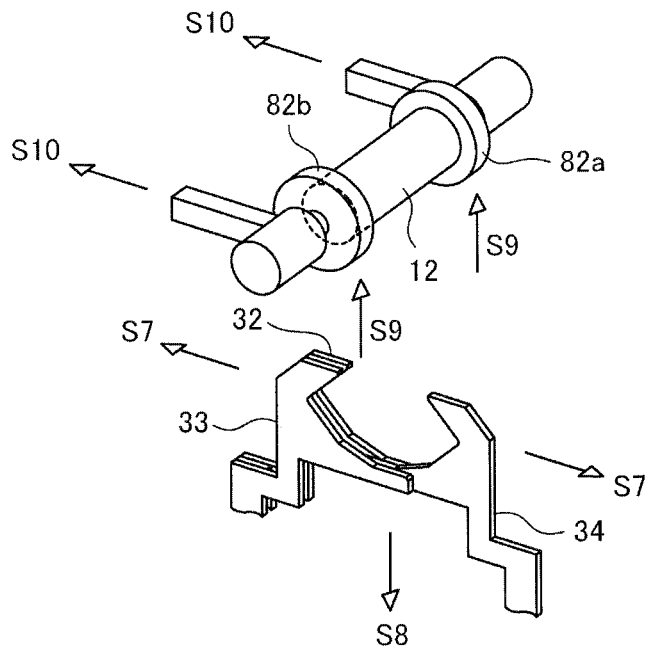
FIGS. 8A and 8B are explanatory views schematically showing the operation example of the information reader of the injection container according to this embodiment.

Next, as shown in FIG. 8A, the pair of the first clamping bodies 32 and 33 and the second clamping body 34 are separated (arrows S7) to release the clamping of the side portions of the injection container 12. Thus, the container rotation supporting mechanism 80 clamps the injection container 12 instead of the container clamping mechanism 30.

Next, as shown in FIG. 8A, the pair of the clamping pads 82a and 82b move up to the predetermined height, while clamping the injection container 12 therebetween (arrows S9). Next, as shown in FIG. 8A, the pair of the clamping pads 82a and 82b are moved horizontally by the horizontal movement unit 140 (arrows S10) while clamping the injection container 12 therebetween, so as to arrange the injection container 12 at the position under the imaging unit 220, as shown in FIG. 8B.

Figure 8B:
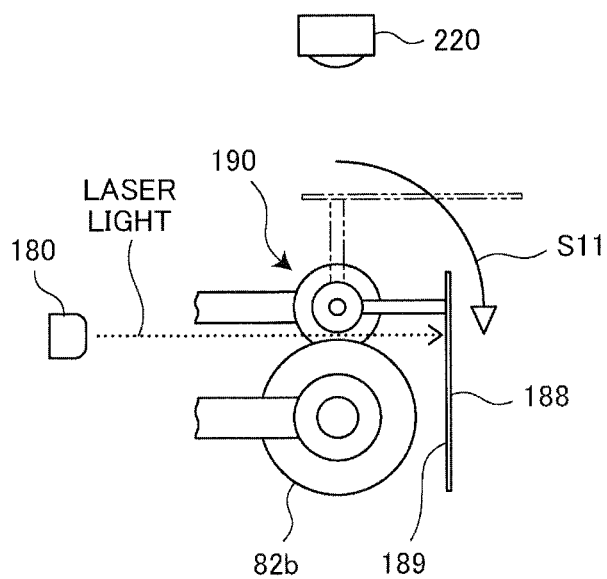

Next, as shown in FIG. 8B, the reflector plate 188 is rotated (arrow S11) by the reflector plate rotating mechanism 190 so as to allow the reflection plane 189 to face against the laser light projecting unit 180.

Figure 9:
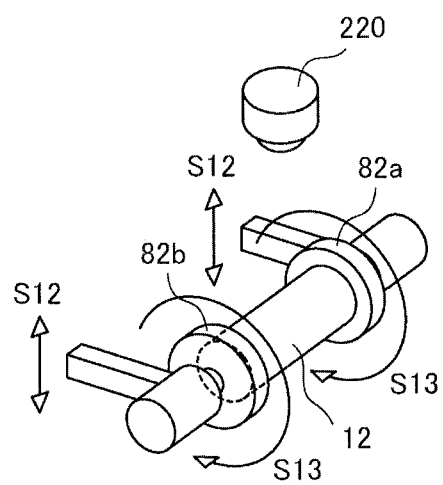
FIG. 9 is an explanatory view schematically showing the operation example of the information reader of the injection container according to this embodiment.

Next, as shown in FIG. 9, the injection container 12 is moved up and down (arrows S12) so that the upper surface of the injection container 12 that is clamped by the container rotation supporting mechanism 80 is adjusted to be approximately level with the height of the laser light (refer to FIG. 8B).

Hereinafter, a concrete example of the adjustment will be explained.

For example, the distance between the laser light projecting unit 180 and the reflector plate 188, where the reflection plane 189 is vertical, is set as the above-described reference distance. When the height of the upper surface of the injection container 12 is lower than the height of the laser light, as shown in FIG. 8B, the laser light passes through the position above the injection container 12 and is reflected by the reflector plate 188. Thus, the laser distance measuring means 187 measures the distance between the laser light projecting unit 180 and the reflector plate 188 as the distance to the target. As the distance to the target is approximately the same as the reference distance in this case, the injection container 12 is moved upward. When the injection container 12 is moved up and the laser light is reflected by the injection container 12, the distance to the target measured by the laser distance measuring means 187 is shorter than the reference distance. Then, the upward movement of the injection container 12 is stopped. Thus, it is possible to adjust the upper surface of the injection container 12 that is clamped by the container rotation supporting mechanism 80 to be approximately level with the height of the laser light.

As described above, the laser light passes through the position below the imaging unit 220 by the subject distance T in the approximately horizontal manner, and therefore, it is possible to arrange the injection container 12 clamped by the container rotation supporting mechanism 80 so that the imaging unit 220 can easily focus on its upper surface, without regard for the shapes of the injection containers 12 and 9.

It should be noted that the information reader 10 of the injection container according to this embodiment includes label recognizing means (not shown) for recognizing the label attached to the outer peripheral surface of the injection container 12. The label is recognized by the label recognizing means while rotating the injection container 12, clamped by the container rotation supporting mechanism 80, about the central axis in the cylinder length direction of the injection container 12, so that the portion where the label is attached on the outer peripheral surface of the injection container 12 can be arranged as the upper surface.

Next, as shown in FIG. 9, while the container rotation supporting mechanism 80 rotates the injection container 12 about a substantially central axis 13 (arrows S13), the imaging unit 220 that is arranged at the position over the injection container 12 captures an image of the outer peripheral surface of the injection container 12. The known pattern matching technique or the like is used to read information of the label from the captured image.

FIG. 11 show areas where the pair of the first clamping bodies and the second clamping body overlap with each other, according to a comparative example and this embed intent.

Figure 11A:
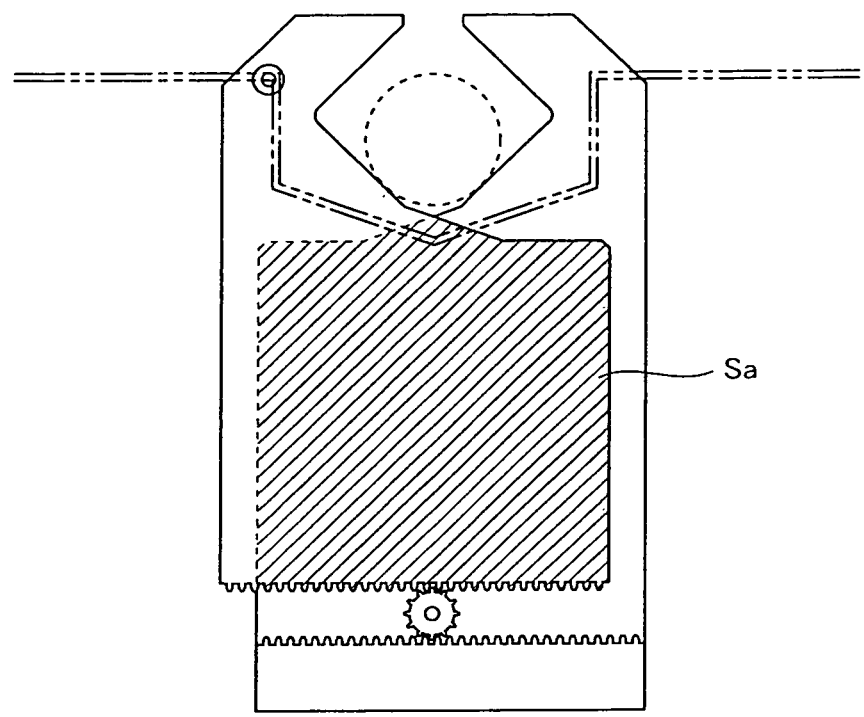
FIG. 11A is an illustration according to the prior art.

FIG. 11A shows the comparative example of Japanese Unexamined Patent Application Publication No. 2010-115339, and a hatched area Sa shows the area where a pair of first clamping bodies and a second clamping body overlap with each other according to the comparative example.

Figure 11B:
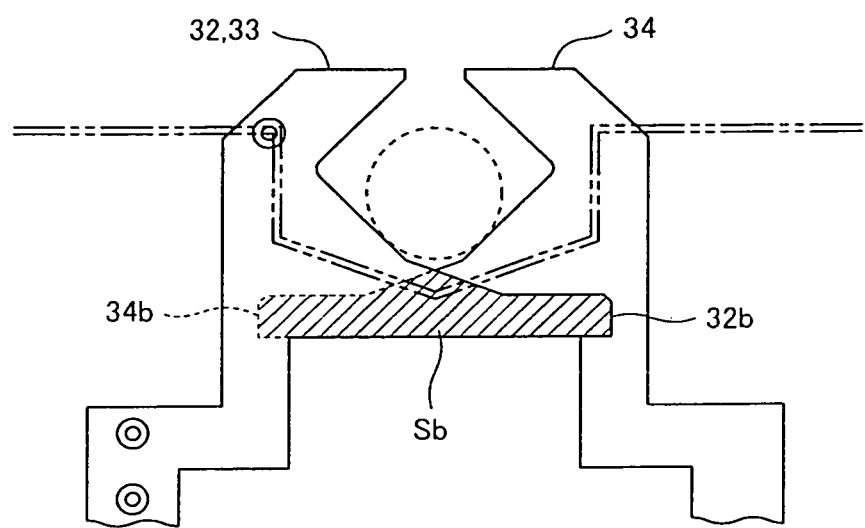
FIG. 11B is an explanatory view schematically explaining effects of the information reader of the injection container according to this embodiment.

Next, FIG. 11B shows this embodiment, and a hatched area Sb shows the area where the pair of the first clamping bodies 32 and 33 and the second clamping body 34 overlap with each other in the information reader 10 of this embodiment.

As described thus far, it is possible for the information reader 10 of this embodiment to reduce the area where the pair of the first clamping bodies 32 and 33 and the second clamping body 34 overlap with each other, because the area where the pair of the first clamping bodies 32 and 33 and the second clamping body 34 overlap with each other at the time of clamping the side portions of the injection containers 9 and 12 mainly consists of the area of the first arm portions 32*b* and 33*b* in a front view added with the area of the second arm portion 34*b* in a front view.

As the area between the first clamping bodies and the second clamping body, into which fragments and wastes enter, can be reduced in the device, it is possible to provide the information reader 10 of the injection container that is capable of suppressing operational malfunctions due to such fragments, wastes and the like.

Some of the embodiments of the present invention have been explained in detail with reference to the drawings. However, the embodiments are for illustrative purposes only. It is possible to embody the invention in other forms with various modifications and improvements based on the knowledge of those skilled in the art.

The invention claimed is:

1. An information reader of an injection container to read information attached on an outer peripheral surface of the injection container in a tubular shape, the information reader of the injection container comprising
    a container clamping mechanism removably clamping side portions of the injection container whose cylinder length direction is made approximately horizontal, wherein the container clamping mechanism comprises
        a pair of first clamping bodies arranged on one side of the side portions of the injection container and arranged to face each other while separating in the cylinder length direction,
        a second clamping body arranged on another side of the side portions of the injection container and capable of entering between the pair of the first clamping bodies, and
        a driving mechanism allowing the pair of the first clamping bodies to advance or retreat in a direction that is the horizontal direction and is almost orthogonal to the cylinder length direction, and allowing the second clamping body to advance or retreat in a direction opposite to the direction of advancing or retreating of the first clamping bodies,
    wherein each of the pair of the first clamping bodies comprises
        a first clamping unit having a first recess in an approximate doglegged shape that bends toward a direction allowing a vertex to separate from the side portion when viewed from the cylinder length direction, and
        a first arm portion projecting approximately horizontally from a lower end portion of the first clamping unit in a direction opposite to the first recess, with its upper edge continuing to a lower end of the first recess,
    wherein the second clamping body comprises
        a second clamping unit having a second recess in an approximately reverse doglegged shape formed to face against the first recess, and
        a second arm portion projecting approximately horizontally from a lower end portion of the second clamping unit in a direction opposite to the second recess, with its upper edge continuing to a lower end of the second recess,
    wherein the driving mechanism allows the pair of the first clamping bodies and the second clamping body that are substantially facing each other to move approachingly and separatingly, and, at a time of approaching, the first arm portion and the second arm portion are overlapped to support the injection container from below, and wherein the driving mechanism comprises an endless belt suspended in the direction of advancing or retreating, wherein the pair of first clamping bodies are coupled to one portion of the endless belt and the second clamping body is coupled to another portion of the endless belt, so that during motion of the endless belt the pair of first clamping bodies move horizontally in a first direction while the second clamping body moves horizontally in a second direction opposite to the first direction, wherein during a first direction of motion of the endless belt the second clamping body and said pair advance toward each other, and during a second direction of motion of the endless belt the second clamping body and said pair retreat away from each other, wherein while the injection container is clamped for reading information attached on the outer peripheral surface of the injection container, the pair of first clamping bodies and the second clamping body are advanced toward each other so that the injection container resides at least in part in the first recess and the second recess, wherein each of the pair of the first clamping bodies further comprises a first leg portion at the lower end portion of the first clamping unit and near an end opposite to the first arm portion, wherein the second clamping body further comprises a second leg portion at the lower end portion of the second clamping unit and near an end opposite to the second arm portion, and wherein the pair of the first leg portions and the second leg portion are respectively connected to the endless belt at opposing positions with a center of rotation therebetween so as to achieve said coupling of the pair of first clamping bodies to said one portion and said second clamping body to said another portion of the endless belt.

* * * * *